United States Patent
Muller et al.

(10) Patent No.: US 10,631,807 B2
(45) Date of Patent: Apr. 28, 2020

(54) METHOD AND APPARATUS FOR CONTRAST-ENHANCED SPECTRAL MAMMOGRAPHY PROGRAMMED SEQUENCES

(71) Applicant: General Electric Company, Schenectady, NY (US)

(72) Inventors: Serge Louis Wilfrid Muller, Buc (FR); Pablo Milioni DeCarvalho, Buc (FR); Ann-Katherine Carton, Buc (FR); Giovanni Palma, Buc (FR); Razvan Iordache, Buc (FR)

(73) Assignee: GENERAL ELECTRIC COMPANY, Schenectady, NY (US)

(*) Notice: Subject to any disclaimer, the term of this patent is extended or adjusted under 35 U.S.C. 154(b) by 0 days.

(21) Appl. No.: 15/624,003

(22) Filed: Jun. 15, 2017

(65) Prior Publication Data
US 2018/0360403 A1 Dec. 20, 2018

(51) Int. Cl.
*A61B 6/00* (2006.01)
*A61B 6/04* (2006.01)
*A61B 6/06* (2006.01)

(52) U.S. Cl.
CPC ............ *A61B 6/481* (2013.01); *A61B 6/0414* (2013.01); *A61B 6/06* (2013.01); *A61B 6/42* (2013.01); *A61B 6/4429* (2013.01); *A61B 6/482* (2013.01); *A61B 6/502* (2013.01); *A61B 6/504* (2013.01); *A61B 6/54* (2013.01)

(58) Field of Classification Search
USPC .............................................. 600/431; 378/62
See application file for complete search history.

(56) References Cited

U.S. PATENT DOCUMENTS

| | | | | |
|---|---|---|---|---|
| 2007/0195932 A1* | 8/2007 | Nakaura | ................ | A61B 6/504 378/98.12 |
| 2010/0061606 A1* | 3/2010 | Geiger | .................. | G06F 19/321 382/128 |
| 2013/0281832 A1* | 10/2013 | Baumgart | ............ | A61B 6/5247 600/424 |
| 2013/0303876 A1* | 11/2013 | Gelfand | ................. | A61B 18/12 600/407 |
| 2016/0341808 A1* | 11/2016 | Zhang | .................. | G01R 33/483 |

* cited by examiner

*Primary Examiner* — Nicole F Lavert
(74) *Attorney, Agent, or Firm* — Fletcher Yoder, P.C.

(57) ABSTRACT

A method of obtaining x-ray images includes controlling operation of an automatic injector to inject a contrast agent into a patient at a predetermined time, synchronizing operations of an x-ray imaging system with the operation of the automatic injector, and obtaining images of a region of interest of the patient during arterial and diffusion phases of the contrast agent.

12 Claims, 9 Drawing Sheets

METHOD AND APPARATUS FOR CONTRAST-ENHANCED SPECTRAL MAMMOGRAPHY PROGRAMMED SEQUENCES

The disclosed exemplary embodiments relate generally to imaging systems, and more particularly to mammography imaging systems.

BACKGROUND

Contrast-enhanced mammography may be used to image the diffusion of blood in interstitial tissue of malignant lesions or tumors. Contrast-enhanced Mammography (CEM) images can be acquired through 1) a temporal sequence of acquisitions using a single x-ray spectrum followed by image subtraction (Temporal-CEM); 2) through a dual or multi-energy sequence using several x-ray spectra followed by recombination of images acquired with different spectra (CESM); or 3) through a temporal sequence of a dual or multi-energy sequence using several x-ray spectra followed by recombination of images acquired with different spectra (Temporal-CESM).

FIG. 1 shows an exemplary Temporal-CEM acquisition process where a pre-injection image (mask image) is acquired using a single x-ray spectrum, followed by an intravenous (IV) injection of a contrast agent, and the acquisition of a series of post-injection images. The pre-injection and post-injection images may typically be acquired with a high energy spectrum compared to a conventional or low energy spectrum typically used in x-ray imaging of the breast (e.g., mammography, digital breast tomosynthesis). The mask image is then log-subtracted from each of the post injection images in order to provide a series of contrast agent images.

FIG. 2 shows an exemplary CESM acquisition process where, after an IV injection of a contrast agent, a series of images are acquired with high energy and low energy x-ray beams. The images acquired at different energies are paired and then recombined to produce a contrast-agent equivalent image, also shown as a "DE" image.

Referring to FIG. 3, a variation of the CESM process, referred to as Temporal-CESM, is illustrated where the high and low energy acquisition process is repeated several times after injection of a contrast agent to deliver a series of DE images that monitors the passage of the contrast agent through anatomical structures of a breast seen under a given incidence and geometry, or to deliver a series of images of one or several breasts under several incidences and/or geometries.

Turning to FIG. 4, assuming the patient's breast is stationary, a series of only high energy images may be acquired over time and the previous low energy images may be used to perform the recombination in order to reduce the x-ray dose delivered to the patient. In cases where the breast may not be stationary, a registration algorithm may be utilized to conform each high energy image to the same reference as the corresponding low energy image.

However, in each of these techniques, because the images are acquired at least a few minutes after IV injection of the contrast agent, the contrast agent is diluted in the patient's blood, and vessels feeding any tumors may not be visible. This is a disadvantage because observing the vessels feeding the tumors provides valuable clinical information. There is ample evidence that the overall vascularity of a tumor is an indicator of the tumor type and grade, but distinguishing between arteries and venous vessels in an image to determine the overall vascularity is often hindered due to the distribution of the contrast agent in the vasculature and the loss of temporal information provided by a first-pass of the contrast agent.

Furthermore, correlation between images acquired during the arterial phase and images acquired during the diffusion in interstitial tissue requires maintaining the breast in the same or similar geometry and position with respect to the imaging components (i.e., x-ray tube and detector). However, the arterial and diffusion phases may be separated by several minutes during which a patient may move, and breast compression may reduce patient comfort and may affect diffusion of the contrast agent in the breast. In addition, operations and procedures by a technologist performing the breast positioning, contrast agent injection, and image acquisition may vary, and those variations may reduce the quantitative content of the acquired images.

There is a need for techniques and devices that enable fast acquisition of high resolution images of an injected breast, and that enable the imaging of the vessels feeding tumors during the arterial phase, with the ability to follow the contrast agent uptake over time.

SUMMARY

The disclosed embodiments are directed to a method of obtaining x-ray images including controlling operation of an automatic injector to inject a contrast agent into a patient at a predetermined time, synchronizing operations of an x-ray imaging system with the operation of the automatic injector, and obtaining images of a region of interest of the patient during arterial and diffusion phases of the contrast agent.

The method may include controlling operation of the automatic injector to inject a specified volume of the contrast agent over a specified time period.

The method may also include synchronizing operations of an x-ray source and an x-ray detector of the x-ray imaging system with the operation of the automatic injector to obtain the images of the region of interest.

The method may further include synchronizing operations of an x-ray source and an x-ray detector of the x-ray imaging system to obtain low energy and high energy images of the region of the interest during the arterial phase.

The method may still further include synchronizing operations of the x-ray imaging system to obtain a recombined arterial phase image from the low energy and high energy images of the region of the interest obtained during the arterial phase.

The method may yet further include synchronizing operations of an x-ray source and an x-ray detector of the x-ray imaging system to obtain low energy and high energy images of the region of the interest during the diffusion phase.

The method may also include synchronizing operations of the x-ray imaging system to obtain a recombined diffusion phase image from the low energy and high energy images of the region of the interest obtained during the diffusion phase.

The method may include synchronizing operations of an x-ray source and an x-ray detector of the x-ray imaging system to obtain a mask image of the region of interest before injection of the contrast agent, obtain single spectrum arterial phase images of the region of interest, and log subtract the mask image from each of the single spectrum arterial phase images to produce a corresponding arterial contrast agent image.

The method may also include synchronizing operations of an x-ray source and an x-ray detector of the x-ray imaging system to obtain single spectrum diffusion phase images of the region of interest, and log subtract the mask image from each of the single spectrum diffusion phase images to produce a corresponding diffusion contrast agent image.

The region of interest may be a patient's breast, and the method may further include synchronizing operations of a compression paddle of the x-ray imaging system with the operation of the automatic injector to obtain images of the breast during arterial and diffusion phases of the contrast agent.

Synchronizing operations of an x-ray imaging system with the operation of the automatic injector to obtain images of a region of interest of the patient during arterial and diffusion phases of the contrast agent, may further include pausing operations to allow for one or more manual procedures, and resuming operations upon completion of the manual procedures.

The disclosed embodiments are also directed to an apparatus for obtaining x-ray images including, an x-ray imaging system configured to obtain images of a region of interest of the patient, an automatic injector configured to inject a contrast agent into a patient, and a programmable synchronization controller having an x-ray imaging system interface and an automatic injector interface for exchanging communications with the x-ray imaging system and the automatic injector, where the programmable synchronization controller is configured to exchange communications for synchronizing operations of the x-ray imaging system with operation of the automatic injector to obtain the images of the region of interest of the patient during arterial and diffusion phases of the contrast agent.

The programmable synchronization controller may be further configured to control the automatic injector to inject a specified volume of the contrast agent over a specified time period.

The programmable synchronization controller may be further configured to exchange communications with the x-ray imaging system and the automatic injector to synchronize operations of an x-ray source and an x-ray detector of the x-ray imaging system with the operation of the automatic injector to obtain the images of the region of interest.

The programmable synchronization controller may also be configured to exchange communications with the x-ray imaging system to synchronize operations of an x-ray source and an x-ray detector of the x-ray imaging system to obtain low energy and high energy images of the region of the interest during the arterial phase.

The programmable synchronization controller may further be configured to exchange communications with the x-ray imaging system to obtain a recombined arterial phase image from the low energy and high energy images of the region of the interest obtained during the arterial phase.

The programmable synchronization controller may also be configured to exchange communications with the x-ray imaging system to synchronize operations of an x-ray source and an x-ray detector of the x-ray imaging system to obtain low energy and high energy images of the region of the interest during the diffusion phase.

The programmable synchronization controller may yet further be configured to exchange communications with the x-ray imaging system to obtain a recombined diffusion phase image from the low energy and high energy images of the region of the interest obtained during the diffusion phase.

The programmable synchronization controller may be configured to exchange communications with the x-ray imaging system to obtain a mask image of the region of interest before injection of the contrast agent, obtain single spectrum arterial phase images of the region of interest, and log subtract the mask image from each of the single spectrum arterial phase images to produce a corresponding arterial contrast agent image.

The programmable synchronization controller may also be configured to obtain single spectrum diffusion phase images of the region of interest, and log subtract the mask image from each of the single spectrum diffusion phase images to produce a corresponding diffusion contrast agent image.

The region of interest may be a patient's breast, and the programmable synchronization controller may be configured to exchange communications with the x-ray imaging system and the automatic injector to synchronize operations of a compression paddle of the x-ray imaging system with the operation of the automatic injector to obtain images of the breast during arterial and diffusion phases of the contrast agent.

The programmable synchronization controller may be configured to pause operations to allow for one or more manual procedures, and resume operations upon completion of the manual procedures.

DETAILED DESCRIPTION

The disclosed embodiments are directed to a system and method for acquiring CEM and CESM images that captures images fast enough to capture the arterial phase information, provides a resolution capable of capturing small vessels feeding tumors that may be present, monitors the passage of the contrast agent through a region of interest, and is capable of monitoring drainage of the contrast agent into the venous vessels. The disclosed embodiments further include the capability of programming various sequences of imaging tasks in order to capture the arterial phase information, provide the desired resolution, monitor the passage of the contrast agent, and monitor the drainage of the contrast agent, while, at the same time, minimizing variations in operator techniques and procedures, variations in breast positioning, and variations in image acquisition timing and techniques.

By implementing a programmable synchronization controller, different tasks can be controlled and synchronized during the course of an imaging procedure, such as: breast compression force or pressure, contrast agent injection (e.g., volume of contrast agent, injection speed, injection timing, etc.), flush of physiological serum, x-ray exposure (e.g., kVp, filter selection, mAs, number of detector frames, etc.), breast decompression, image recombination, image display, and other tasks related to mammography imaging.

Figure 1:
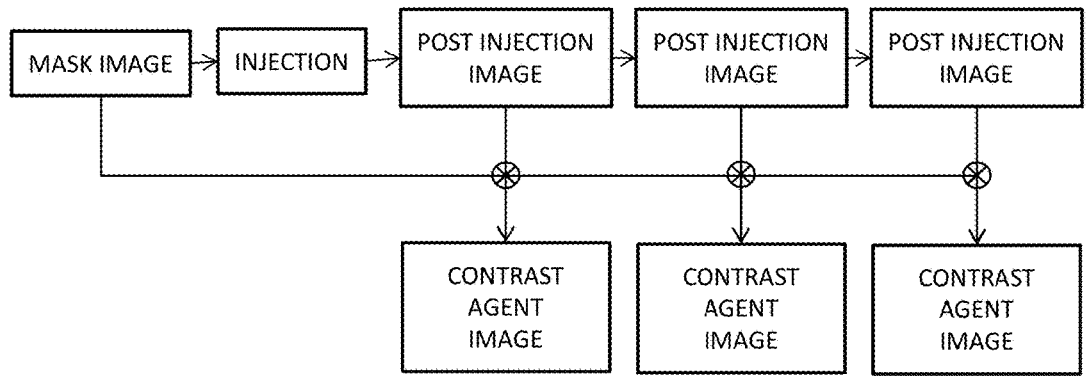
FIG. 1 shows an exemplary Temporal-CEM image acquisition process.
Figure 2:
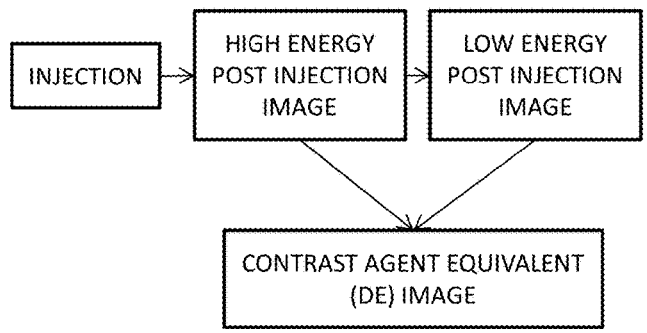
FIG. 2 shows an exemplary CESM image acquisition process.
Figure 3:
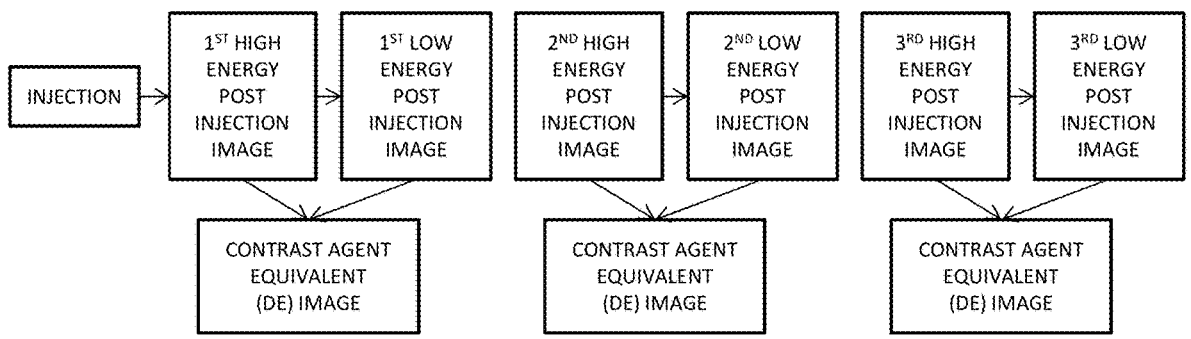
FIG. 3 shows an exemplary Temporal-CESM image acquisition process.
Figure 4:
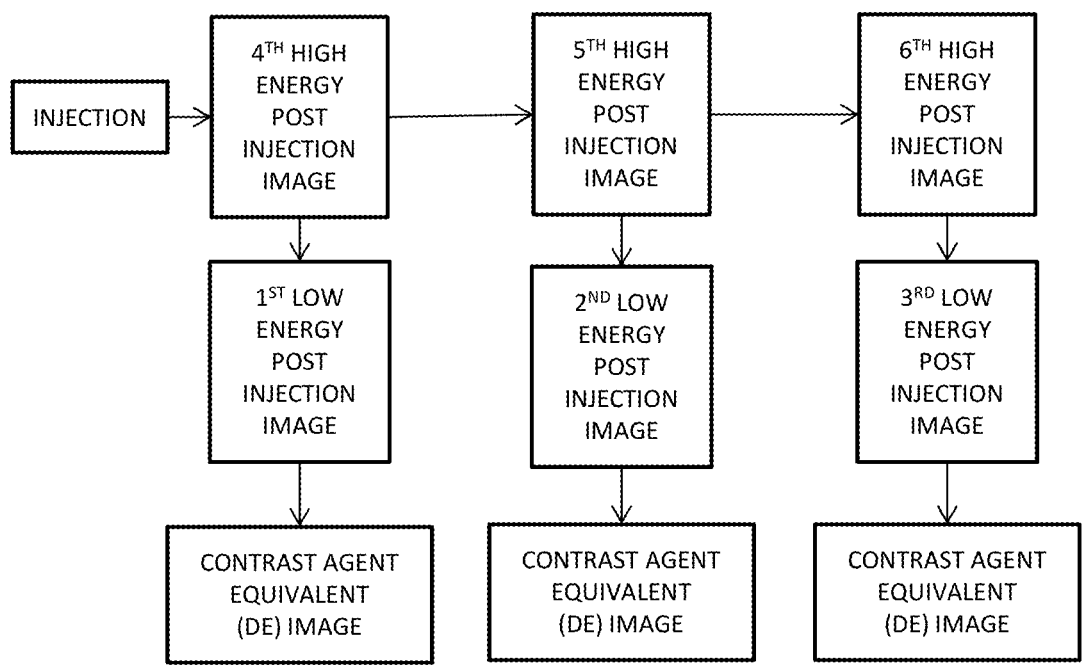
FIG. 4 shows an exemplary imaging process where only high energy images may be acquired over time and previous low energy images may be used to perform a recombination.
Figure 5:
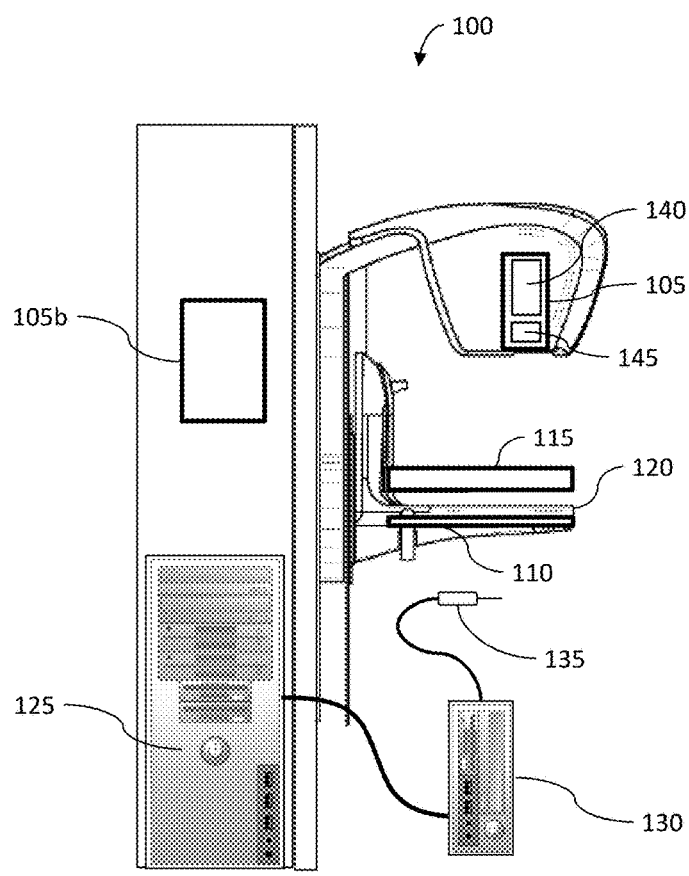
FIG. 5 shows an exemplary mammography imaging system according to the disclosed embodiments.

FIG. 5 shows an exemplary mammography imaging system 100 for acquiring mammography images, including temporal contrast enhanced mammography images, contrast-enhanced spectral mammography images and temporal contrast-enhanced spectral mammography images, according to the disclosed embodiments. The mammography imaging system 100 may include an x-ray source 105, an x-ray detector 110, a compression paddle 115, a support table 120, a system controller 125, a programmable synchronization controller 130, and an automatic injector 135 which may be remotely controlled by the programmable synchronization controller 130. In some embodiments, the programmable synchronization controller 130 and automatic injector 135 may be retrofitted to a pre-existing mammography imaging system.

Figure 6:
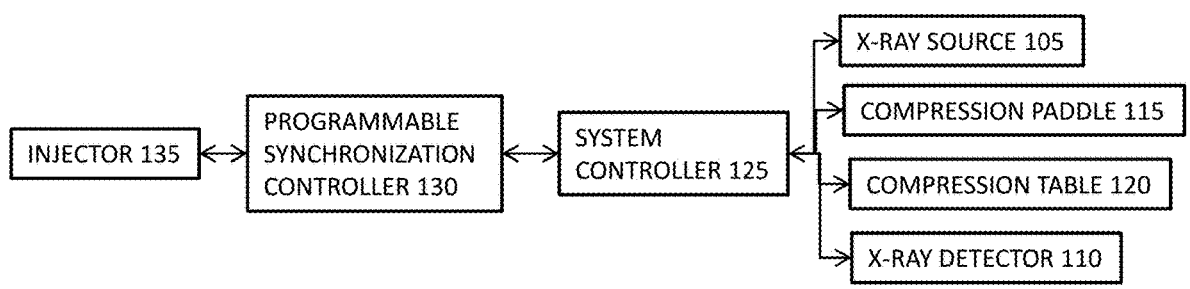
FIG. 6 illustrates various connections among different system components.

FIG. 6 illustrates the various connections among the different system components. According to the disclosed embodiments, the programmable synchronization controller 130 may exchange commands with the system controller 125 to control the x-ray source 105, x-ray detector 110, compression paddle 115, and support table 120, and may exchange commands with the automatic injector 135. By controlling the system components 125, 105, 110, 115, 120, and 135, the programmable synchronization controller 130 may operate to standardize x-ray imaging operations, synchronize operations among the mammography system components, and eliminate delays and variations in procedures due to operator delays and differences in following procedures. It should be understood that the locations of the system components 125, 105, 110, 115, 120, and 135, and the programmable synchronization controller 130, are shown for illustrative purposes only and that the components may be remotely located, may be integrated together, or may have any combination of a remote and integrated configuration.

The X-ray source 105 may include an X-ray tube 140 connected to an X-ray generator 105b that can be embedded in a tube head or in any other place including, for example, the mammography gantry or the exam room, and a collimator 145. The x-ray detector 110 may be a digital radiography receiver panel and may have a two dimensional detection plane for detecting X-rays. The x-ray detector 110 may have a relatively high resolution and a high acquisition rate. In some exemplary embodiments, a suitable detector may have a resolution of approximately 2048×2048, or higher, with a pixel pitch of approximately 200 um or lower, and a relatively fast image acquisition rate, such as less than 1 sec., with a repetition rate of less than 10 sec. Other suitable resolutions and acquisition rates may also be used so long as the X-ray detector 110 is capable of providing a resolution that allows capturing images of small vessels feeding a tumor and a rate that allows capturing the filling of arterial vessels, monitoring the passage of a contrast agent through the tumor, as well as drainage through the venous vessels. For example, CMOS detector technology is a potential enabler for such an X-ray detector implementation, because it provides both fast acquisition capability and high resolution images required to capture small vessels.

The detector 110 may communicate with the system controller 125 and may provide image data from scanning procedures in real time. In some embodiments, the detector 110 may have a wireless communication capability and may be coupled wirelessly to the system controller 125. In one or more embodiments, the detector 110 may store imaging data and output the imaging data when subsequently coupled to the controller 125.

The compression paddle 115 may be movable in vertical and horizontal directions under control of the system controller 125 and may operate to compress a patient's breast against the support table 120. The support table 120 may provide a stable platform for breast compression, and in some embodiments, the support table 120 may also be movable, for example, to accommodate patients with different heights.

Figure 7:
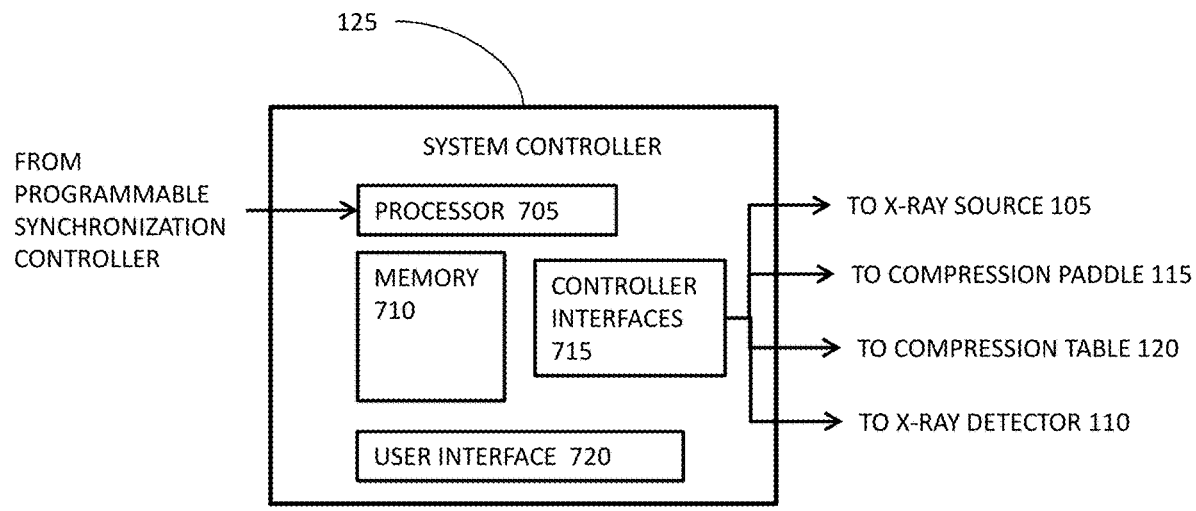
FIG. 7 shows a block diagram of an exemplary system controller.

Referring to FIG. 7, the system controller 125 may include a processor 705, a memory 710, and one or more controller interfaces 715. The system controller 125 may receive commands from the programmable synchronization controller 130 for controlling the X-ray source 105, the detector 110, the compression paddle 115 and the support table 120. The one or more controller interfaces 715 may exchange signals and communications with the various components of the mammography system 100 and with other systems that may be remote from the mammography system 100. For example, the controller 125 may transmit image data to another remote system for review and analysis. The system controller 125 may also include a user interface 720 to allow operator input and to provide output to an operator. For example, the user interface 720 may include a display device or hard copy device for displaying or outputting images obtained according to the disclosed embodiments, to an operator or other personnel for analysis.

Figure 8:
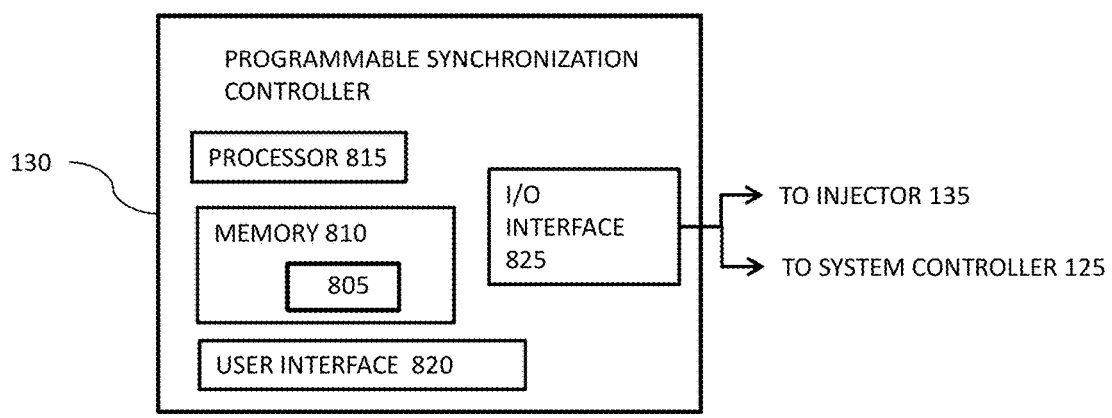
FIG. 8 shows a block diagram of an exemplary programmable synchronization controller according to the disclosed embodiments.

FIG. 8 shows a block diagram of the programmable synchronization controller 130. The programmable synchronization controller 130 may include computer readable program code 805 stored on at least one computer readable medium 810 for carrying out and executing the process steps described herein. The computer readable medium 810 may be a memory of the programmable synchronization controller 130. The programmable synchronization controller 130 may have a processor 815 for executing the computer readable program code 805. The programmable synchronization controller 130 may include one or more input or output devices, referred to as a user interface 820, which may operate to allow user input to the programmable synchronization controller 130 or to provide output to a user. In addition, the user interface 820 may include a display device or hard copy device, similar to the user interface 720 of the system controller 125, for displaying or outputting images obtained according to the disclosed embodiments, to an operator or other personnel for analysis. Furthermore, the programmable synchronization controller 130 may also include an input/output interface 825 for exchanging communications among the automatic injector 135 and the system controller 125. The communications may include providing control signals to the automatic injector 135 and the system controller 125 for controlling and coordinating the functions of the automatic injector 135 and the system controller 125.

The programmable synchronization controller 130 may provide commands to the automatic injector 135. The automatic injector 135 may include a needle and one or more syringes or other fluid metering systems and a mechanism for operating the metering systems for injecting a specified amount of fluid over a specified time period. In at least one embodiment, the automatic injector 135 may be pre-loaded with a contrast agent, and may receive commands from the programmable synchronization controller 130 regarding an amount of contrast agent to be injected over a particular time period. In one or more embodiments, the automatic injector 135 may have a plurality of barrels for injecting more than one fluid, for example, a contrast agent and a saline solution. In other embodiments, the automatic injector 135 may have a plurality of interconnected injector mechanisms for injecting more than one fluid. The automatic injector 135 and may receive communications from the programmable synchronization controller 130 regarding amounts of fluid to be injected over particular time periods.

The programmable synchronization controller 130 may also provide commands to the system controller 125 for controlling a frequency and amount of radiation produced by the X-ray source 105, the sensitivity of the detector 110, and the movement of the compression paddle 115 and the support table 120.

Figure 9A:
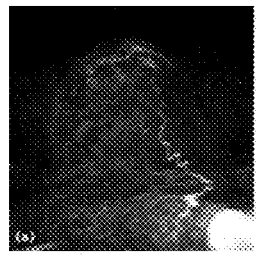
FIG. 9A shows an image of a contrast agent during a filling of arterial vessels during an arterial phase.
Figure 9B:
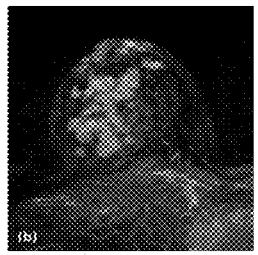
FIG. 9B shows the passage of a contrast agent through a region of interest.
Figure 9C:
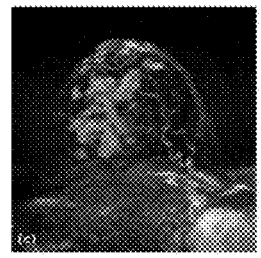
FIG. 9C shows the drainage of the contrast agent into venous vessels.

FIG. 9A shows an image of a contrast agent during a filling of arterial vessels during an arterial phase, FIG. 9B shows the passage of a contrast agent through a region of interest, and FIG. 9C shows the drainage of the contrast agent into venous vessels. As shown in FIG. 9A, it would be advantageous to capture the contrast agent during the filling of arterial vessels during an arterial phase that may extend for a period of time, for example, up to approximately 30 seconds after contrast agent injection. As shown in FIGS. 9B and 9C, it would also be advantageous to monitor the passage of the contrast agent through a region of interest, for example, a tumor or inflammatory carcinoma, and to monitor drainage of the contrast agent into the venous vessels, which in some applications may take several minutes.

Figure 10:
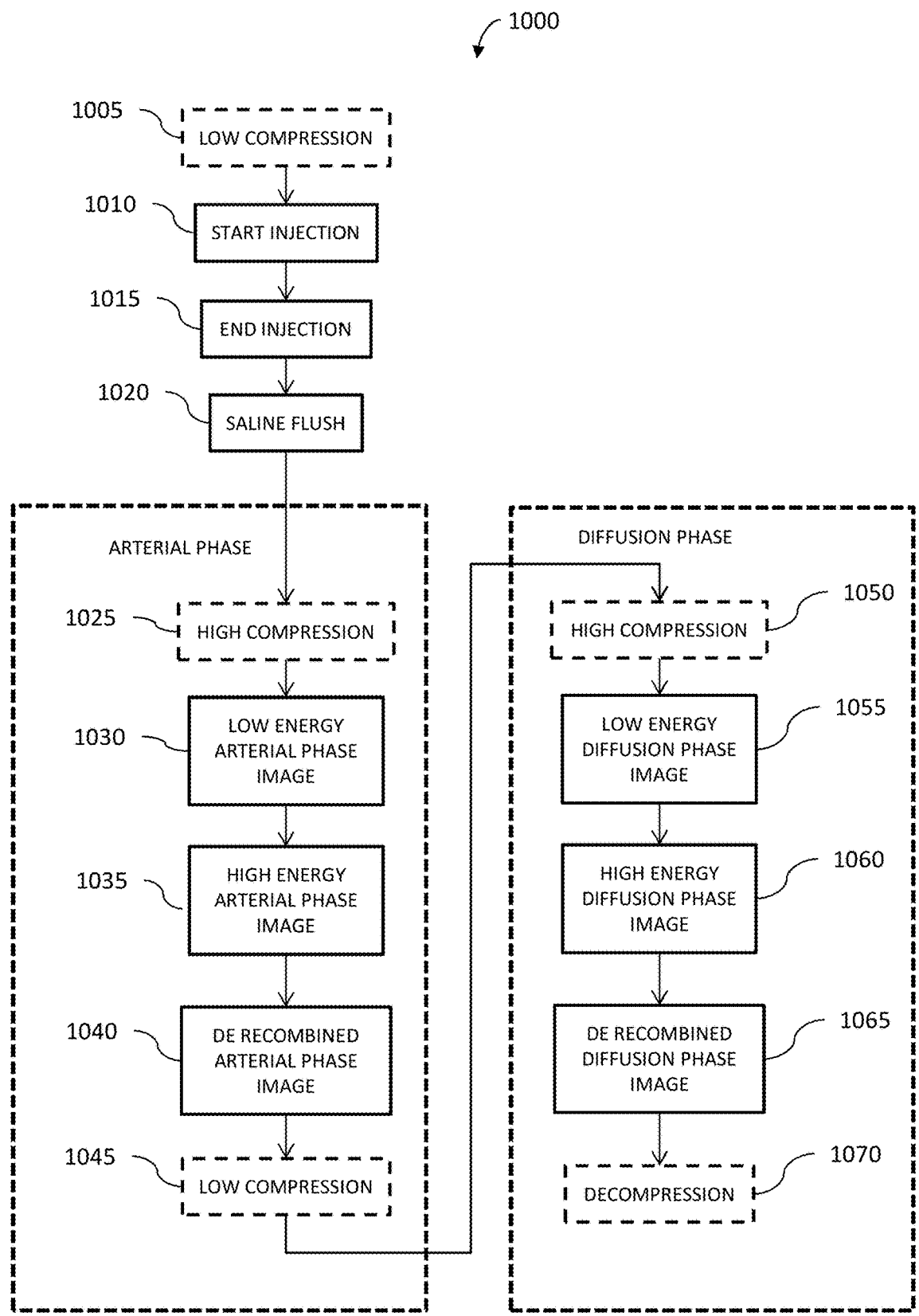
FIG. 10 illustrates an example of a possible fully automated sequence of tasks for a Temporal CESM image acquisition process according to the disclosed embodiments.

FIG. 10 illustrates an example of a possible fully automated sequence of tasks 1000 that could be programmed into, and controlled by, the programmable synchronization controller 130 to realize a Temporal-CESM imaging procedure of a patient breast including the imaging of the contrast agent during arterial and diffusion phases. The programmable synchronization controller 130 may be programmed to cause each of the system components 125, 105, 110, 115, 120, and 135, to perform the operations shown in each block.

In block 1005, the compression paddle 115 may provide a low compressive force to a patient's breast. In block 1010, the automatic injector 135 may start an injection of contrast agent at a specified rate of delivery. In block 1015, the automatic injector 135 may stop the injection of contrast agent, and in block 1020, the automatic injector 135 may perform a saline flush to expel the remaining contrast agent.

The compression paddle 115 may provide a high compressive force to a patient's breast in block 1025, and the x-ray source 105 and x-ray detector 110 may operate to acquire a low energy arterial phase image in block 1030. In block 1035, the x-ray source 105 and x-ray detector 110 may be controlled to acquire a high energy arterial phase image, and in block 1040, the low energy arterial phase image and high energy arterial phase image may be recombined to produce a DE arterial phase image. The compression paddle 115 may provide a low compressive force to a patient's breast in block 1045.

When the programmable synchronization controller 130 has determined that the diffusion phase has begun, the programmable synchronization controller 130 may cause the compression paddle 115 to provide a high compressive force to the patient's breast in block 1050, and may cause the x-ray source 105 and x-ray detector 110 to acquire a low energy diffusion phase image in block 1055. In block 1060, the x-ray source 105 and x-ray detector 110 may be controlled to acquire a high energy diffusion phase image, and in block 1065, the low energy diffusion phase image and high energy diffusion phase image may be recombined to produce a DE diffusion phase image. The compression paddle 115 may retract and allow the patient's breast to decompress in block 1070.

In some embodiments, the imaging procedure 1000 may be accomplished without the low compression, high compression, and decompression operations 1005, 1025, 1045, 1050, 1070. In one or more embodiments, in order to compensate for movement caused by applying different compression forces to the breast, or to compensate for motion caused by patient movement, a registration algorithm may be employed to realign the reference frame of the high energy arterial phase image 1035 with that of the corresponding low energy arterial phase image 1030, and to realign the reference frame of the high energy diffusion phase image 1060 with that of the corresponding low energy diffusion phase image 1055.

Figure 11A:
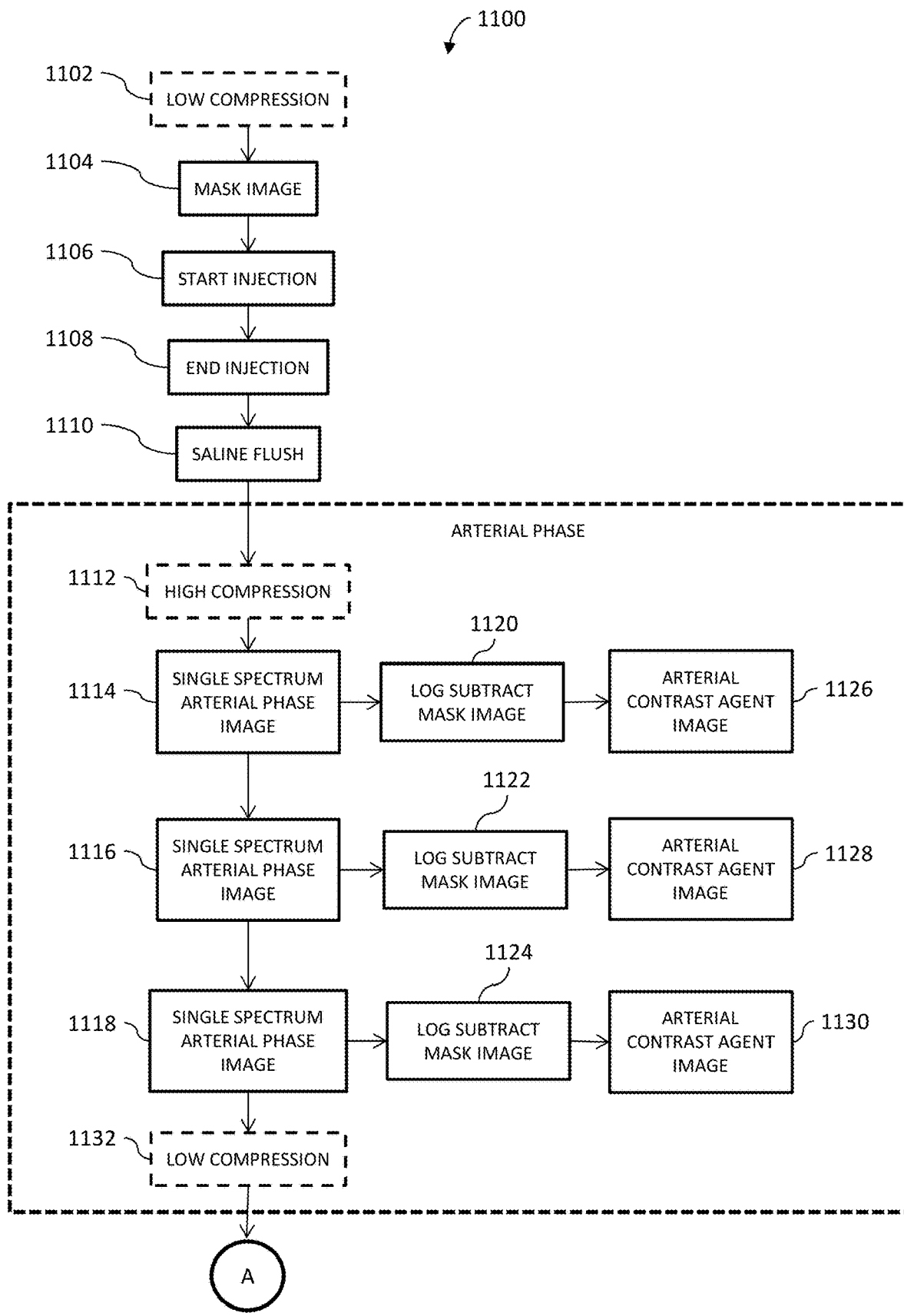
FIGS. 11A and 11B illustrate an example of a possible fully automated sequence of tasks for a Temporal CEM acquisition process according to the disclosed embodiments.
Figure 11B:
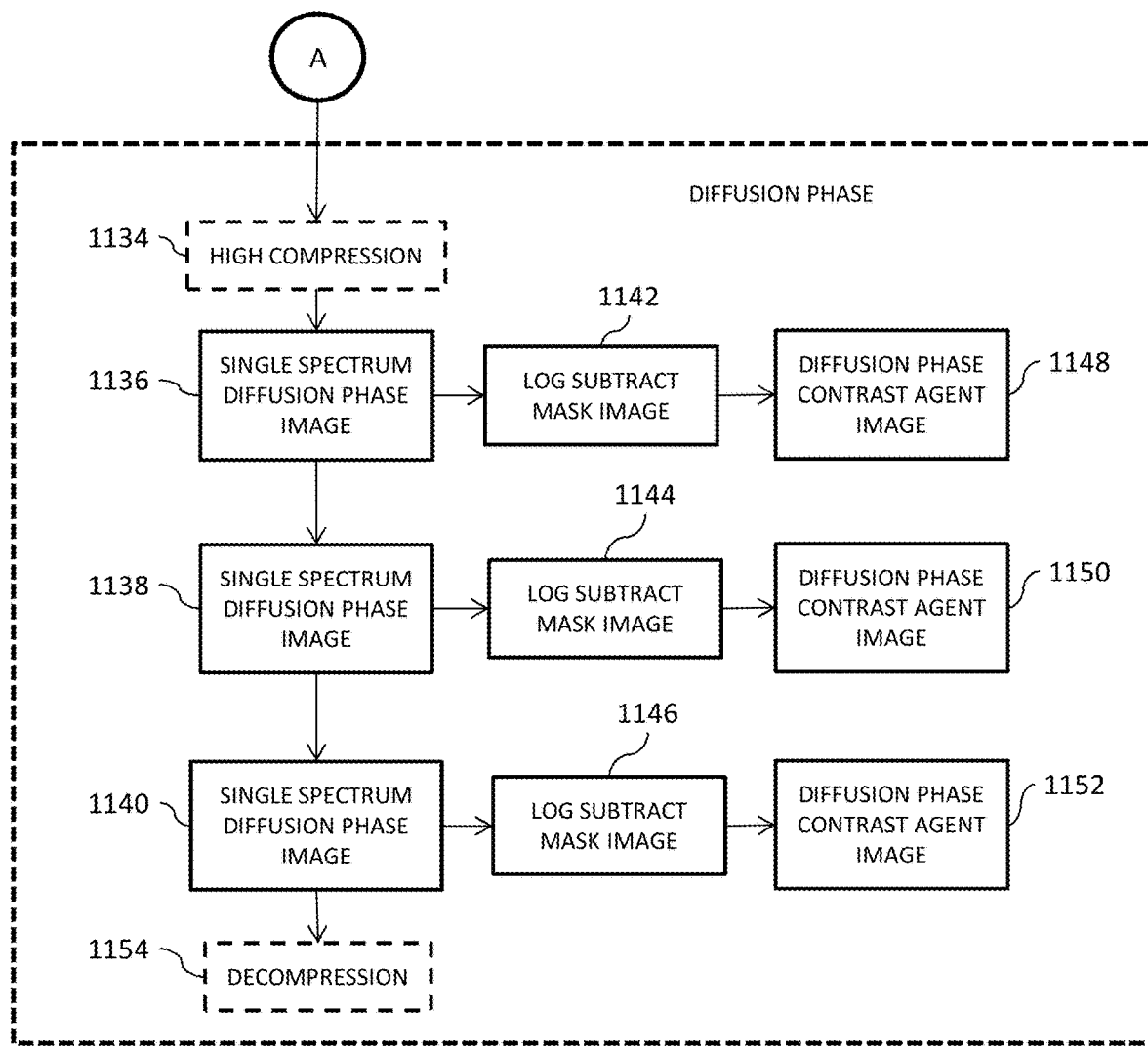

FIGS. 11A and 11B illustrate an example of a possible fully automated sequence of tasks 1000 that could be programmed into, and controlled by, the programmable synchronization controller 130 to realize a Temporal-CEM imaging procedure of a patient breast including the imaging of the contrast agent during arterial and diffusion phases. The programmable synchronization controller 130 may be programmed to cause each of the system components 125, 105, 110, 115, 120, and 135, to perform the operations shown in each block.

In block 1102, the compression paddle 115 may provide a low compressive force to a patient's breast. In block 1104, a mask image of the breast may be taken. In block 1106, the automatic injector 135 may start an injection of contrast agent at a specified rate of delivery. In block 1108, the automatic injector 135 may stop the injection of contrast agent, and in block 1110, the automatic injector 135 may perform a saline flush to expel the remaining contrast agent.

The compression paddle 115 may provide a high compressive force to a patient's breast in block 1112, and the x-ray source 105 and x-ray detector 110 may operate to acquire single spectrum arterial phase images in blocks 1114, 1116, 1118. The mask image may then be subtracted from each of the single spectrum arterial phase images, as shown in blocks 1120, 1122, 1124. As a result, a corresponding arterial phase contrast agent image 1126, 1128, 1130 may be generated. The compression paddle 115 may then provide a low compressive force to a patient's breast in block 1132.

When the programmable synchronization controller 130 has determined that the diffusion phase has begun, the programmable synchronization controller 130 may cause the compression paddle 115 to provide a high compressive force to the patient's breast in block 1134, and may cause the x-ray source 105 and x-ray detector 110 to acquire single spectrum diffusion phase images in blocks 1136, 1138, 1140. The mask image is then log subtracted from each of the single spectrum diffusion phase images, as shown in blocks 1142, 1144, 1146. As a result, a corresponding diffusion contrast agent image 1148, 1150, 1152 may be generated. The compression paddle 115 may retract and allow the patient's breast to decompress in block 1154.

Similar to the imaging procedure 1000, in some embodiments, the imaging procedure 1100 may be accomplished without the low compression, high compression, and decompression operations 1102, 1112, 1132, 1134, 1154. In one or more embodiments, in order to compensate for movement caused by applying different compression forces to the breast, or to compensate for motion caused by patient movement, a registration algorithm may be employed to realign the mask image with the single spectrum arterial phase images 1114, 1116, 1118 or to realign the mask image with the single spectrum diffusion phase images 1136, 1138.

Figure 12:
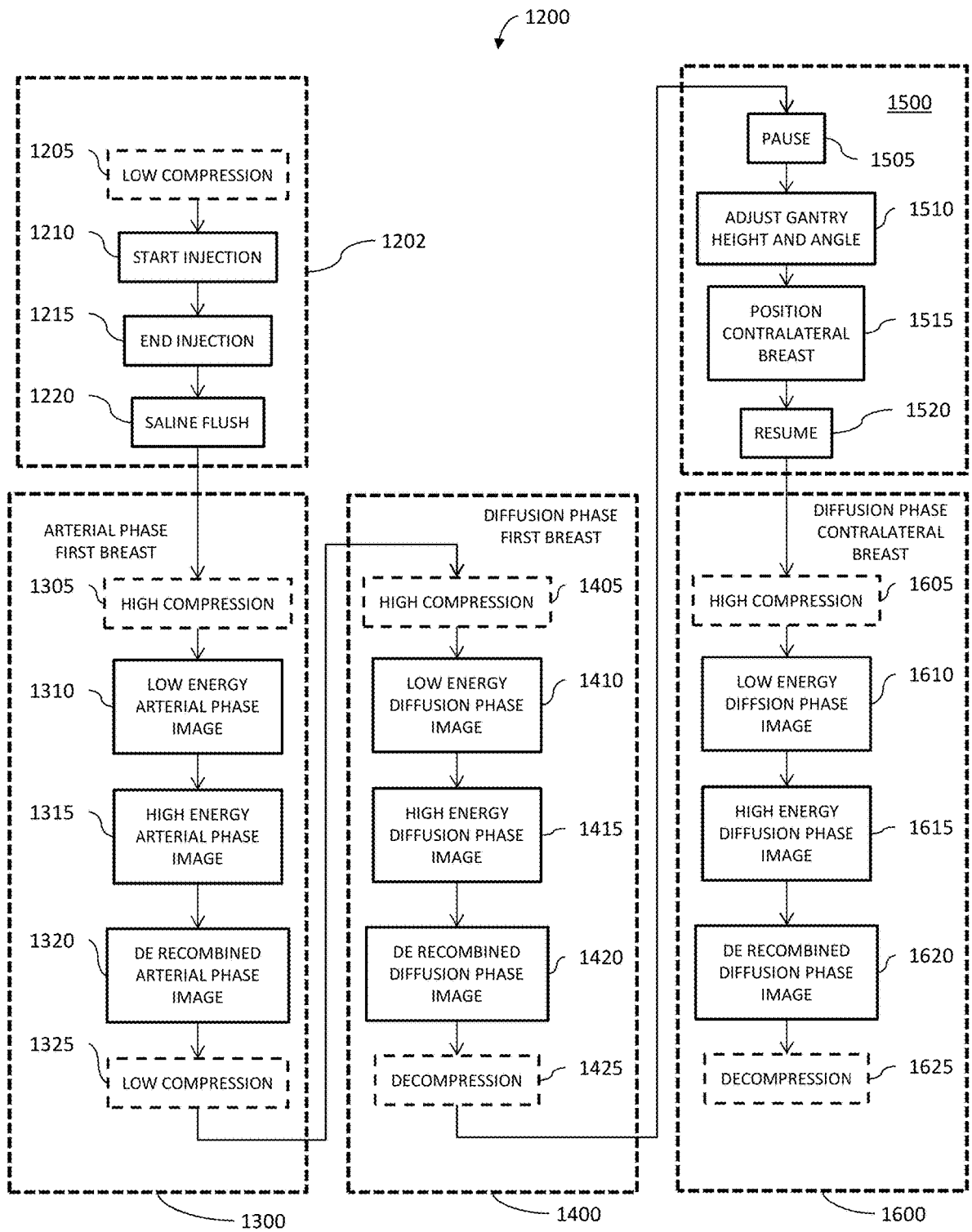
FIG. 12 illustrates an example of a sequence of imaging acquisition tasks that include both automated preprogrammed tasks and manual procedures, according to the disclosed embodiments.

FIG. 12 illustrates an example of a possible sequence of tasks 1200 that include both automated preprogrammed tasks that may be controlled over a specific time period, as well as manual procedures that may be difficult to control within a specific time period or may require patient interaction over a time period that may be hard to predict. In this example, the programmable synchronization controller 130 may be programmed to allow for both programmed and manual procedures during CESM imaging of the arterial phase of a patient's first (left or right) breast that may include a suspected lesion, followed by imaging of the diffusion phase of the same breast and then by imaging of the diffusion phase of the patient's second or contralateral breast. The programmable synchronization controller 130 may be programmed to cause each of the system components 125, 105, 110, 115, 120, and 135, to perform the operations shown in each automated task block as well as being programmed to pause for manual intervention and then resume when commanded by an operator. In this example, tasks 1202, 1300, 1400, and 1600 may be automated by the programmable synchronization controller 130, while procedures 1500 may be manual.

In block 1205, the compression paddle 115 may provide a low compressive force to a patient's breast. In block 1210, the automatic injector 135 may start an injection of contrast agent at a specified rate of delivery. In block 1215, the automatic injector 135 may stop the injection of contrast agent, and in block 1220, the automatic injector 135 may perform a saline flush to expel the remaining contrast agent.

The compression paddle 115 may provide a high compressive force to the patient's first breast in block 1305, and the x-ray source 105 and x-ray detector 110 may operate to acquire a low energy arterial phase image in block 1310. In block 1315, the x-ray source 105 and x-ray detector 110 may be controlled to acquire a high energy arterial phase image, and in block 1320, the low energy arterial phase image and high energy arterial phase image may be recombined to produce a DE arterial phase image of the first breast. The compression paddle 115 may provide a low compressive force to the patient's first breast in block 1325.

When the programmable synchronization controller 130 has determined that the diffusion phase in the first breast has begun, the programmable synchronization controller 130 may cause the compression paddle 115 to provide a high compressive force to the patient's first breast in block 1405, and may cause the x-ray source 105 and x-ray detector 110 to acquire a low energy diffusion phase image in block 1410. In block 1415, the x-ray source 105 and x-ray detector 110 may be controlled to acquire a high energy diffusion phase image, and in block 1420, the low energy diffusion phase image and high energy diffusion phase image may be recombined to produce a DE diffusion phase image of the first breast. The compression paddle 115 may retract and allow the patient's breast to decompress in block 1425.

After the diffusion phase imaging of the first breast is complete, the programmable synchronization controller 130 may be programmed to pause and wait for a command to resume in order to allow for one or more manual procedures, as shown in block 1505. In this example, the operator may adjust the height and angle of a gantry of the mammography imaging system 100, as shown in block 1510 and, as shown in block 1515, may position the patient's contralateral breast for imaging. The programmable synchronization controller 130 may then receive a command to resume programmed operations, as shown in block 1520.

After receiving a command to resume, when the programmable synchronization controller 130 has determined that the diffusion phase has begun in the contralateral breast, the programmable synchronization controller 130 may cause the compression paddle 115 to provide a high compressive force to the patient's contralateral breast in block 1605, and may cause the x-ray source 105 and x-ray detector 110 to acquire a low energy diffusion phase image in block 1610. In block 1615, the x-ray source 105 and x-ray detector 110 may be controlled to acquire a high energy diffusion phase image, and in block 1620, the low energy diffusion phase image and high energy diffusion phase image may be recombined to produce a DE diffusion phase image of the contralateral breast. The compression paddle 115 may retract and allow the patient's contralateral breast to decompress in block 1625.

As mentioned above with respect to the imaging procedures 1000, 1100, in some embodiments, the imaging procedure 1200 may be accomplished without the low compression 1205, 1325, high compression 1305, 1405, 1605, and decompression 1425, 1625 operations. In at least one embodiment, compensation for movement caused by applying different compression forces to the breast, or compensation for motion caused by patient movement, may be effected using a registration algorithm to realign the reference frame of the high energy arterial phase image 1315 with the reference frame of the corresponding low energy arterial phase image 1310, and to realign the reference frames of the high energy diffusion phase images 1415, 1615 with the reference frames of the corresponding low energy diffusion phase images 1410, 11610, respectively.

The present invention provides for new clinical imaging capabilities by allowing clinicians to collect information about the arterial phase of contrast uptake in contrast-enhanced mammography with the potential to improve clinical accuracy.

The invention, thanks to high spatial and temporal resolution capabilities of the detector, allows imaging of the smallest vessels feeding the lesion which are not visible on CESM images.

The invention allows for the reduction of the variability in CEM acquisition sequences. It enables the succession of a series of tasks to be executed within a short duration thanks to a programmable synchronization module that acts as an orchestrator for the different devices involved during the CEM imaging procedure.

The invention claimed is:

1. A method of obtaining x-ray images comprising:
controlling operation of an automatic injector to inject a contrast agent into a patient at a predetermined time;

synchronizing operations of an x-ray imaging system with the operation of the automatic injector;

obtaining a first plurality of images of a region of interest of the patient during an arterial phase of the contrast agent, wherein the first plurality of images comprises low energy and high energy images of the region of interest during the arterial phase;

processing the low energy and high energy images from the first plurality of images to obtain a recombined arterial phase image;

obtaining a second plurality of images of the region of interest of the patient during a diffusion phase of the contrast agent, wherein the second plurality of images comprises low energy and high energy images of the region of interest during the diffusion phase; and processing the low energy and high energy images from the second plurality of images to obtain a recombined diffusion phase image.

2. The method of claim 1, further comprising controlling operation of the automatic injector to inject a specified volume of the contrast agent over a specified time period.

3. The method of claim 1, further comprising synchronizing operations of an x-ray source and an x-ray detector of the x-ray imaging system with the operation of the automatic injector to obtain the images of the region of interest.

4. The method of claim 1, wherein the region of interest is a patient's breast, and the method further comprises synchronizing operations of a compression paddle of the x-ray imaging system with the operation of the automatic injector to obtain images of the breast during the arterial and diffusion phases of the contrast agent.

5. The method of claim 1, wherein synchronizing operations of an x-ray imaging system with the operation of the automatic injector to obtain images of the region of interest of the patient during the arterial and diffusion phases of the contrast agent further comprises:

pausing operations to allow for one or more manual procedures; and resuming operations upon completion of the manual procedures.

6. An apparatus for obtaining x-ray images comprising:

an x-ray imaging system configured to obtain images of a region of interest of the patient;

an automatic injector configured to inject a contrast agent into a patient; and a programmable synchronization controller comprising an x-ray imaging system interface and an automatic injector interface for exchanging communications with the x-ray imaging system and the automatic injector, wherein the programmable synchronization controller is configured to exchange communications for synchronizing operations of the x-ray imaging system with operation of the automatic injector to:

obtain a first plurality of images of the region of interest of the patient during an arterial phase of the contrast agent, wherein the first plurality of images comprises low energy and high energy images of the region of interest during the arterial phase;

process the low energy and high energy images from the first plurality of images to obtain a recombined arterial phase image;

obtain a second plurality of images of the region of interest of the patient during a diffusion phase of the contrast agent, wherein the second plurality of images comprises low energy and high energy images of the region of interest during the diffusion phase; and process the low energy and high energy images from the second plurality of images to obtain a recombined diffusion phase image.

7. The apparatus of claim 6, wherein the programmable synchronization controller is further configured to control the automatic injector to inject a specified volume of the contrast agent over a specified time period.

8. The apparatus of claim 6, wherein the programmable synchronization controller is further configured to exchange communications with the x-ray imaging system and the automatic injector to synchronize operations of an x-ray source and an x-ray detector of the x-ray imaging system with the operation of the automatic injector to obtain the images of the region of interest.

9. The apparatus of claim 6, wherein the region of interest is a patient's breast, and the programmable synchronization controller is further configured to exchange communications with the x-ray imaging system and the automatic injector to synchronize operations of a compression paddle of the x-ray imaging system with the operation of the automatic injector to obtain the images of the breast during the arterial and/or diffusion phases of the contrast agent.

10. The apparatus of claim 6, wherein the programmable synchronization controller is further configured to pause operations to allow for one or more manual procedures, and resume operations upon completion of the manual procedures.

11. A method of obtaining x-ray images comprising:

controlling operation of an automatic injector to inject a contrast agent into a patient at a predetermined time;

synchronizing operations of an x-ray imaging system with the operation of the automatic injector;

obtaining a mask image of a region of interest of the patient before injection of the contrast agent;

obtaining a first plurality of images of the region of interest of the patient during an arterial phase of the contrast agent, wherein the first plurality of images comprises single spectrum arterial phase images of the region of interest; and log subtracting the mask image from each of the single spectrum arterial phase images to produce a corresponding arterial contrast agent image.

12. The method of claim 11, comprising:

obtain a second plurality of images of the region of interest of the patient during a diffusion phase of the contrast agent, wherein the second plurality of images comprises single spectrum diffusion phase images of the region of interest; and log subtracting the mask image from each of the single spectrum diffusion phase images to produce a corresponding diffusion contrast agent image.

* * * * *